United States Patent
Kawashima et al.

(10) Patent No.: US 6,869,984 B2
(45) Date of Patent: Mar. 22, 2005

(54) DENTAL COMPOSITION KIT

(75) Inventors: Mitsunobu Kawashima, Kurashiki (JP); Ikuo Omura, Kurashiki (JP); Mayumi Yamashita, Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 402 days.

(21) Appl. No.: 10/171,596

(22) Filed: Jun. 17, 2002

(65) Prior Publication Data

US 2003/0083398 A1 May 1, 2003

(30) Foreign Application Priority Data

Jun. 28, 2001 (JP) .......................... 2001-195703

(51) Int. Cl.$^7$ .......................... A61K 6/083; C08K 3/34
(52) U.S. Cl. .................. 523/116; 523/115; 523/118; 524/443; 526/277; 106/35
(58) Field of Search .................. 523/115, 116, 523/118; 524/535; 526/277; 106/35

(56) References Cited

U.S. PATENT DOCUMENTS

| | | | |
|---|---|---|---|
| 4,182,035 A | 1/1980 | Yamauchi et al. | |
| 4,539,382 A | 9/1985 | Omura et al. | |
| 4,816,495 A | 3/1989 | Blackwell et al. | |
| 5,063,257 A | 11/1991 | Akahane et al. | |
| 5,130,347 A | 7/1992 | Mitra | |
| 5,367,002 A | 11/1994 | Huang et al. | |
| 5,520,725 A | 5/1996 | Kato et al. | |
| 5,760,101 A | 6/1998 | Heiliger et al. | |
| 5,808,104 A | 9/1998 | Podszun et al. | |

FOREIGN PATENT DOCUMENTS

| | | |
|---|---|---|
| JP | 2-6358 | 1/1990 |
| JP | 2-164807 | 6/1990 |
| JP | 03-240712 | * 10/1991 |
| JP | 5-255033 | 10/1993 |
| JP | 9025208 | * 7/1995 |
| JP | 8-26925 | 1/1996 |
| JP | 9-249514 | 9/1997 |
| JP | 10-505868 | 6/1998 |
| JP | 10-506127 | 6/1998 |

OTHER PUBLICATIONS

Patent Abstracts of Japan, JP 2000–026225, Jan. 25, 2000.
Quintessence International, vol. 16, No. 4 (1997) pp69–72, Glass–ionomer Cement Restorations and Secondary Caries: A Preliminary Report (with English Translation).

* cited by examiner

*Primary Examiner*—Tae H. Yoon
(74) *Attorney, Agent, or Firm*—Oblon, Spivak, McClelland, Maier & Neustadt, P.C.

(57) ABSTRACT

The invention refers to a dental composition kit which comprises a combination of (A) a one-pack primer composition containing (a) an acid group-having polymerizable monomer and (b) an aromatic secondary amine and/or an aromatic tertiary amine, and (B) a cement composition containing (c) a polyalkenoic acid, (d) an ion-leachable glass filler, (e) a polymerizable monomer, (f) water, (g) a peroxide and (h) a salt of an aromatic sulfinic acid. A dental composition kit of this invention is easy to handle, and the cured product of the compositions bonds well to teeth. The kit is useful in restoring decayed or injured teeth and in bonding prostheses to teeth.

12 Claims, No Drawings

DENTAL COMPOSITION KIT

BACKGROUND OF THE INVENTION

1. Field of the Invention

The present invention relates to a dental composition kit. Precisely, the invention relates to a dental composition kit, of which the cured product of the compositions well bonds to hard tissues such as tooth enamel in dentin, and which is therefore useful in restoring decayed or injured teeth and in bonding prostheses to teeth.

2. Description of the Related Art

For restoring decayed or injured teeth, widely used are amalgam, glass ionomer cement and composite resin. On the other hand, for bonding prostheses such as crowns, inlays and bridges to decayed or injured teeth, widely used are zinc phosphate cement, glass ionomer cement and composite resin cement. In that manner, various materials are used for restoring decayed or injured teeth, and one of them is glass ionomer cement.

The basic constituent components of glass ionomer cement are a polyalkenoic acid, water and an ion-leachable glass filler. Improving the properties of such glass ionomer cement by adding thereto some other components has been tried, for example, as in Japanese Patent Laid-Open Nos. 164807/1990, 6358/1990, 255033/1993, 26925/1996, and International Patent Publication Nos. 505868/1998, 506127/1998. The improved glass ionomer cement of those types is generally referred to as resin-modified glass ionomer cement, and has become popular in the recent year.

The basic principle in restoration of defective teeth is to fill an aesthetic material of certain strength in the cavity of defective teeth or in the space between a defective tooth and a prosthesis to thereby ensure the permanent function of the restored teeth, not to merely improve the function and the shape of the restored teeth for the moment, and it is to further ensure the prevention of caries recurring.

In general, it is known that glass ionomer cement releases fluorine effective for making teeth acid resistant from the viewpoint of caries prevention, but it should be understood that the fluorine release from it is only an auxiliary function of glass ionomer cement. Specifically, if the cause of secondary caries is not eliminated, fluorine release, if any, to reinforce teeth could not be the essential solution of caries. For essentially solving the problem of caries, it is first necessary to surely seal up the interface between a restored tooth and a prosthesis with cement. This is to prevent caries-causing bacteria from invading the aforesaid interface and to prevent food residues that may be the nutrients for the bacteria also from entering it, to thereby prevent secondary caries recurring. For it, the function of fluorine may be taken into consideration merely as an auxiliary preventive means for bonding failure in the restored tooth. As so reported in the *Quintessence*, Vol. 16, No. 4 (1997), pp. 69–72, secondary caries accounts for about 50% of the reason for re-restoration of teeth once restored with glass ionomer cement, and is significant. This is because of mistaking the means for the end in that fluorine only is expected for caries prevention.

In restoring decayed or injured teeth, it is desired to establish tight adhesion of a restorative to a tooth. For a technique increasing the bonding power of resin-modified glass ionomer cement to teeth, for example, Japanese Patent Laid-Open No. 249514/1997 discloses a primer composition.

Regarding the primer technique such as that disclosed in the laid-open patent specification, it is known that a combination of an organic peroxide, amine and a salt of a sulfinic acid is an effective polymerization initiator in bonding restoratives to teeth. However, when the constitutive ingredients of the initiator, an organic peroxide, amine and a salt of a sulfinic acid are blended in a primer, the primer must be a two-pack primer, as in the examples in Japanese Patent Laid-Open No. 249514/1997. Such a two-pack primer is troublesome in dental use in that the two packs must be mixed every time before use. If the two packs are mixed and the resulting mixture is left as it is for a while for some reason in dental treatment, the mixture will soon polymerize and cure, and will be useless. Even if the mixture does not polymerize to such an extent that it cure, the reaction of the constitutive ingredients progresses and the mixture will lose its effective function for bonding.

Further, the bonding power of dental cement to teeth is not indiscriminately determined only by the primer composition between the cement and a tooth. Specifically, the total composition of primer and cement must be taken into consideration to attain a higher level bonding of cement to teeth, because the reactivity of the two affect not a little the bonding power of cement to teeth.

To solve the problems noted above, we, the present inventors have assiduously studied various primer and cement compositions, especially the type of polymerization initiator to be used in the compositions and how the polymerization initiator is to be incorporated into them, and, as a result, have found a dental composition kit comprising a one-pack primer composition and a cement composition. When combinatorially used, the two compositions of the kit give high bond strength of restorative to tooth. On the basis of this finding, we have completed the present invention.

SUMMARY OF THE INVENTION

The invention refers to a dental composition kit, which comprises a combination of (A) a one-pack primer composition containing (a) an acid group-having polymerizable monomer and (b) an aromatic secondary amine and/or an aromatic tertiary amine, and (B) a cement composition containing (c) a polyalkenoic acid, (d) an ion-leachable glass filler, (e) a polymerizable monomer, (f) water, (g) a peroxide and (h) a salt of an aromatic sulfinic acid.

The dental composition kit of the invention is easy to handle. When combinatorially used, the two compositions of the kit give high bond strength of restoratives to teeth. Therefore, the kit is useful not only as cement for bonding restorative prostheses to decayed or injured teeth but also as cement for constructing abutment. In addition, it is useful as a sealant to occlusal surfaces and as a coating material for root surfaces.

DETAILED DESCRIPTION OF THE PREFERRED EMBODIMENTS

The invention is described in detail hereinunder.

The acid group-having polymerizable monomer (a) for use in the invention is indispensable for ensuring the bonding power of the cement composition to teeth. The polymerizable monomer has at least one acid group of, for example, a phosphoric acid group, pyrophosphoric acid group, carboxylic acid group, sulfonic acid group or thiophosphoric acid group, and has a polymerizable unsaturated group such as an acryloyl group, methacryloyl group, vinyl group or styrene group. Examples of the compounds are mentioned below. (Meth)acryl is meant to include methacryl and acryl.

Examples of the phosphoric acid group-having polymerizable monomers are 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, di[2-(meth)acryloyloxyethyl] hydrogen phosphate, di[4-(meth)acryloyloxybutyl] hydrogen phosphate, di[6-(meth)acryloyloxyhexyl] hydrogen phosphate, di[8-(meth)acryloyloxyoctyl] hydrogen phosphate, di[9-(meth)acryloyloxynonyl] hydrogen phosphate, di[10-(meth)acryloyloxydecyl] hydrogen phosphate, 1,3-di (meth)acryloyloxypropyl-2 dihydrogen phosphate, 2-(meth)acryloyloxyethylphenyl hydrogen phosphate, 2-(meth)acryloyloxyethyl 2'-bromoethyl hydrogen phosphate, 2-(meth)acryloyloxyethyl phenyl phosphonate; (5-methacryloxy)pentyl-3-phosphonopropionate, (6-methacryloxy)hexyl-3-phosphonopropionate, (10-methacryloxy)decyl-3-phosphonopropionate, (6-methacryloxy)hexyl-3-phosphonoacetate, (10-methacryloxy)decyl-3-phosphonoacetate; 2-methacryloyloxyethyl 4-methoxyphenyl hydrogen phosphate, 2-methacryloyloxypropyl 4-methoxyphenyl hydrogen phosphate, glycerol phosphate di(meth)acrylate, dipentaerythritol phosphate penta(meth)acrylate; and their acid chlorides.

Examples of the pyrophosphoric acid-having polymerizable monomers are di[2-(meth)acryloyloxyethyl] pyrophosphate, di[4-(meth)acryloyloxybutyl] pyrophosphate, di[6-(meth)acryloyloxyhexyl] pyrophosphate, di[8-(meth)acryloyloxyoctyl] pyrophosphate, di[10-(meth)acryloyloxydecyl] pyrophosphate; and their acid chlorides.

Examples of the carboxylic acid group-having polymerizable monomers are maleic acid, methacrylic acid, 4-[(meth)acryloyloxyethoxycarbonyl]phthalic acid, 4-[(meth)acryloyloxybutyloxycarbonyl]phthalic acid, 4-[(meth)acryloyloxyhexyloxycarbonyl]phthalic acid, 4-[(meth)acryloyloxyoctyloxycarbonyl]phthalic acid, 4-[(meth)acryloyloxydecyloxycarbonyl]phthalic acid, and their acid anhydrides; 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, 11-(meth)acryloyloxy-1,1-undecanedicarboxylic acid; and their acid chlorides.

Examples of the sulfonic acid group-having polymerizable monomers are 2-(meth)acyrlamido-2-methylpropanesulfonic acid, styrenesulfonic acid, 2-sulfoethyl (meth)acrylate; and their acid chlorides.

Examples of the thiophosphoric acid group-having polymerizable monomers are 10-(meth)acryloyloxydecyl dihydrogen dithiophosphate and its acid chlorides.

Of those acid group-having polymerizable monomers, preferred are phosphoric acid or thiophosphoric acid group-having polymerizable monomers as the cement composition combined with the monomer of the type well bonds to teeth and prostheses. More preferred are polymerizable monomers of the following general formula (I); and even more preferred are those of the following general formula (II) and/or (III).

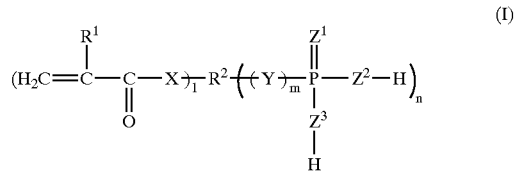

wherein $R^1$ represents a hydrogen atom or a methyl group; $R^2$ represents an organic group having from 2 to 40 carbon atoms; X represents a group of —O— or —NH—; l indicates an integer of from 1 to 5; m indicates an integer of 0 or 1; n indicates an integer of from 1 to 4; Y represents a group of —O— or —S—; and $Z^1$, $Z^2$ and $Z^3$ each represent an oxygen atom or a sulfur atom.

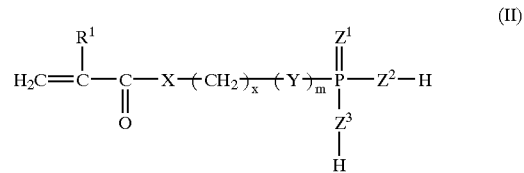

wherein $R^1$ represents a hydrogen atom or a methyl group; X represents a group of —O— or —NH—; x indicates an integer of from 4 to 20; m indicates an integer of 0 or 1; Y represents a group of —O— or —S—; and $Z^1$, $Z^2$ and $Z^3$ each represent an oxygen atom or a sulfur atom.

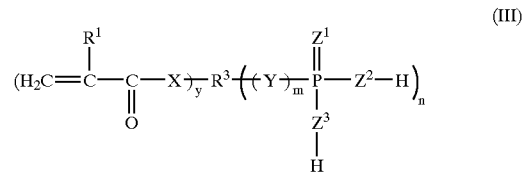

wherein $R^1$ represents a hydrogen atom or a methyl group; $R^3$ represents an organic group having from 3 to 10 carbon atoms; X represents a group of —O— or —NH—; y indicates an integer of from 2 to 5; m indicates an integer of 0 or 1; n indicates an integer of from 1 to 4; Y represents a group of —O— or —S—; and $Z^1$, $Z^2$ and $Z^3$ each represent an oxygen atom or a sulfur atom.

In formula (I), $R^2$ represents an organic group having from 2 to 40 carbon atoms, and is preferably an alkyl group having from 2 to 40 carbon atoms. In formula (III), $R^3$ represents an organic group having from 3 to 10 carbon atoms, and is preferably an alkyl group having from 3 to 10 carbon atoms.

The aromatic secondary amine and/or aromatic tertiary amine (b) for use in the invention includes, for example, N-methylaniline, N-methyl-p-toluidine, N-methyl-m-toluidine, N-methyl-o-toluidine, N-ethanol-p-toluidine, N-ethanol-m-toluidine, N-ethanol-o-toluidine, ethyl p-methylaminobenzoate, ethyl m-methylaminobenzoate, ethyl o-methylaminobenzoate, p-methylaminoanisole, m-methylaminoanisole, o-methylaminoanisole, 1-methylaminonaphthalene, 2-methylaminonaphthalene, N,N-dimethylaniline, N,N-dimethyl-p-toluidine, N,N-dimethyl-m-toluidine, N,N-dimethyl-o-toluidine, N,N-diethanol-p-toluidine, N,N-diethanol-m-toluidine, N,N-diethanol-o-toluidine, ethyl p-dimethylaminobenzoate, ethyl m-dimethylaminobenzoate, ethyl o-dimethylaminobenzoate, p-dimethylaminoanisole, m-dimethylaminoanisole, O-dimethylaminoanisole, 1-dimethylaminonaphthalene, 2-dimethylaminonaphthalene.

The polyalkenoic acid (c) for use in the invention is an organic polymer having a carboxyl group or any other acid group capable of reacting with the cation released by the ion-leachable glass filler (d) to form a poly-salt. The filler (d) is described in detail hereinunder. Preferably, the acid (c) is a polymer of an unsaturated monocarboxylic acid or an unsaturated dicarboxylic acid, including, for example, homopolymers of acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, and copolymers of such unsaturated carboxylic acids with other comonomers. In the copolymers, the proportion of the unsaturated carboxylic acid units is preferably at least 50 mol % to the total constitutive units. The comonomers are preferably ethylenic unsaturated polymerizable comonomers, including, for example, styrene, acrylamide, acrylonitrile, methyl methacrylate, salts of acrylic acid, vinyl chloride, allyl chloride, vinyl acetate, 1,1,6-trimethylhexamethylene dimethacrylate. Of those polyalkenoic acids, preferred are homopolymers and copolymers of acrylic acid or maleic acid. If the weight-average molecular weight of the polyalkenoic acid is not higher than 5,000, the strength of the cured product of the cement composition containing the acid will be low and the durability thereof may become poor. On the other hand, if the weight-average molecular weight of the polyalkenoic acid is higher than 40,000, the viscosity of the cement composition containing the acid will be too high to manipulate the cement composition in clinical practice, and the workability thereof will be poor. Accordingly, it is desirable that the polyalkenoic acid has a weight-average molecular weight of from 5,000 to 40,000.

The ion-leachable glass filler (d) for use in the invention releases divalent or more polyvalent cations of, for example, strontium, calcium, zinc, aluminium, iron or zirconium capable of reacting with the polyalkenoic acid (c). Concretely, it includes, for example, fluoroaluminosilicate glass, calcium fluoroaluminosilicate glass, strontium fluoroaluminosilicate glass, barium fluoroaluminosilicate glass, and strontium calcium fluoroaluminosilicate glass. Of those, preferred are fluoroaluminosilicate glass and barium fluoroaluminosilicate glass. If the mean particle size of the ion-leachable glass filler is larger than 20 μm, the surface of the cured product of the cement composition containing the filler of such coarse particles will be roughened and will therefore has a rough feel, and, in addition, the workability of the cement composition will be poor. On the other hand, if the mean particle size of the ion-leachable glass filler is smaller than 0.02 μm, the amount of the filler of such fine particles that may be mixed with other liquid ingredients to formulate cement compositions will be low and, if so, the physical properties of the cement composition containing the filler of such fine particles will be not good. Accordingly, it is desirable that the ion-leachable glass filler has a mean particle size of from 0.02 to 20 μm.

If desired, the ion-leachable glass filler (d) may be previously surface-treated with any known surface-treating agent such as a silane coupling agent. The surface-treating agent includes, for example, vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, γ-aminopropyltriethoxysilane.

The polymerizable monomer (e) for use in the invention is not specifically defined, including, for example, the acid group-having polymerizable monomers (a) mentioned hereinabove and polymerizable monomers (i) not having an acid group such as those mentioned below. The polymerizable monomers (i) not having an acid group are grouped into hydrophilic polymerizable monomers and non-hydrophilic polymerizable monomers. Not only one but also two or more different types of such polymerizable monomers may be used herein either singly or in combination. "Hydrophilic" is meant to indicate that the solubility in water at 25° C. of the monomers is at least 10% by weight, preferably at least 30% by weight.

The hydrophilic polymerizable monomers are, for example, 2-hydroxyethyl (meth)acrylate, 2-hydroxypropyl (meth)acrylate, 3-hydroxypropyl (meth)acrylate, 1,3-dihydroxypropyl (meth)acrylate, 2,3-dihydroxypropyl (meth)acrylate, dipentaerythritol di(meth)acrylate, (meth)acrylamide, 2-hydroxyethyl(meth)acrylamide, polyethylene glycol di(meth)acrylates (having at least 9 oxyethylene groups).

The non-hydrophilic polymerizable monomers are, for example, esters such as α-cyanoacrylates, (meth)acrylates, α-halogenoacrylates, crotonates, cinnamates, sorbates, maleates, itaconates; and (meth)acrylamide derivatives, vinyl esters, vinyl ethers, mono-N-vinyl derivatives, styrene derivatives. Of those, preferred are (meth)acrylates.

Examples of the non-hydrophilic polymerizable monomers usable in the invention are mentioned below. Monomers having one olefinic double bound in the molecule are referred to as monofunctional monomers; and those having two or more olefinic double bonds in the molecule are referred to as difunctional, trifunctional or more polyfunctional monomers depending on the number of the olefinic double bonds therein.

Monofunctional Monomers:

Methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2,3-dibromopropyl (meth)acrylate, 3-methacryloyloxypropyltrimethoxysilane, 11-methacryloyloxyundecyltrimethoxysilane.

Difunctional Monomers:

Ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, 2,2-bis[4-(meth)acryloyloxyethoxyphenyl]propane, 2,2-bis[4-(meth)acryloyloxypolyethoxyphenyl]propane, 2,2-bis[4-[3-(meth)acryloyloxy-2-hydroxypropoxy]phenyl]-propane, 1,2-bis[3-(meth)acryloyloxy-2-hydroxypropoxy]ethane, pentaerythritol di(meth)acrylate, 1,2-bis(3-methacryloyloxy-2-hydroxypropoxy)ethane, [2,2,4-trimethylhexamethylenebis(2-carbamoyloxyethyl)]di(meth)acrylate, 1,3-di(meth)acryloyloxy-2-hydroxypropane.

Trifunctional or more Polyfunctional Monomers:

Trimethylolpropane tri(meth)acrylate, trimethylolethane tri(meth)acrylate, tetramethylolmethane tri(meth)acrylate, pentaerythritol tetra(meth)acrylate, N,N'-(2,2,4-trimethylhexamethylene)bis[2-(aminocarboxy)-propane-1,3-diol] tetramethacrylate, 1,7-diacryloyloxy-2,2,6,6-tetraacryloyloxymethyl-4-oxyheptane.

Water (f) for use in the invention may be any one not containing impurities that may have some negative influences on the curability of the cement composition and on the bonding power of the cured product of the cement composition to teeth, for which, however, preferred is distilled water or ion-exchanged water.

The peroxide (g) for use in the invention includes, for example, diacyl peroxides, peroxyesters, dialkyl peroxides, peroxyketals, ketone peroxides, hydroperoxides. Concretely, the diacyl peroxides include benzoyl peroxide, 2,4-dichlorobenzoyl peroxide, m-toluoyl peroxide, lauroyl peroxide. The peroxyesters include, for example, t-butylperoxy benzoate, bis-t-butylperoxy isophthalate, 2,5-dimethyl-2,5-bis(benzoylperoxy)hexane, t-butylperoxy 2-ethylhexanoate, t-butylperoxyisopropyl carbonate. The dialkyl peroxides include, for example, dicumyl peroxide, di-t-butyl peroxide. The peroxyketals include, for example, 1,1-bis(t-butylperoxy)-3,3,5-trimethylcyclohexane, 1,1-bis(t-butylperoxy)cyclohexane, 1,1-bis(t-hexylperoxy) cyclohexane. The ketone peroxides include, for example, methyl ethyl ketone peroxide, cyclohexanone peroxide, methyl acetacetate peroxide. The hydroperoxides include, for example, t-butyl hydroperoxide, cumene hydroperoxide, p-diisopropylbenzene peroxide.

The salt of an aromatic sulfinic acid (h) for use in the invention includes, for example, lithium salts, sodium salts, potassium salts, rubidium salts, cesium salts, magnesium salts, calcium salts, strontium salts, iron salts, copper salts, zinc salts, ammonium salts, tetramethylammonium salts and tetraethylammonium salts of benzenesulfinic acid, p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid, chlorobenzenesulfinic acid, naphthalenesulfinic acid.

The dental composition kit of the invention comprises a combination of the one-pack primer composition (A) that contains the acid group-having polymerizable monomer (a) and the aromatic secondary amine and/or aromatic tertiary amine (b), and the cement composition (B) that contains the polyalkenoic acid (c), the ion-leachable glass filler (d), the polymerizable monomer (e), water (f), the peroxide (g) and the salt of an aromatic sulfinic acid (h).

In the primer composition (A), the content of the acid group-having polymerizable monomer (a) is preferably from 1 to 90% by weight, more preferably from 5 to 70% by weight. Not only one but also two or more different types of acid group-having polymerizable monomers (a) may be in the composition.

Preferably, the content of the aromatic secondary amine and/or aromatic primary amine (b) in the primer composition (A) is from 0.1 to 20% by weight, more preferably from 1 to 10% by weight. Not only one but also two or more different types of secondary aromatic amines and/or aromatic tertiary amines (b) may be in the composition.

If desired, the primer composition (A) may additionally contain water and/or a volatile organic solvent having a boiling point not higher than 150° C., preferably not higher than 100° C. at normal pressure. The solvent includes, for example, alcohols such as ethanol, methanol, 1-propanol, isopropyl alcohol; ketones such as acetone, methyl ethyl ketone; esters such as ethyl acetate, methyl acetate, ethyl propionate; ethers such as 1,2-dimethoxyethane, 1,2-diethoxyethane, tetrahydrofuran; hydrocarbon compounds such as heptane, hexane, toluene; and halogenohydrocarbon compounds such as chloroform, dichloromethane. The content of water and/or the volatile organic solvent, if any, in the primer composition (A) is preferably from 0.1 to 80% by weight, more preferably from 0.5 to 70% by weight.

The primer composition (A) may further contain the polymerizable monomer (i) not having an acid group. The content of the polymerizable monomer (i), if any, in the primer composition (A) is preferably from 1 to 80% by weight, more preferably from 5 to 50% by weight.

The content of the polyalkenoic acid (c) in the cement composition (B) is preferably from 0.5 to 50% by weight, more preferably from 1 to 20% by weight. Not only one but also two or more different types of polyalkenoic acids (c) may be in the composition.

Preferably, the content of the ion-leachable glass filler (d) in the cement composition (B) is from 10 to 90% by weight, more preferably from 20 to 80% by weight. Not only one but also two or more different types of ion-leachable glass fillers (d) may be in the composition.

Also preferably, the content of the polymerizable monomer (e) in the cement composition (B) is from 1 to 70% by weight, more preferably from 5 to 50% by weight. Not only one but also two or more different types of polymerizable monomers (e) may be in the composition.

Also preferably, the content of water (f) in the cement composition (B) is from 1 to 50% by weight, more preferably from 5 to 30% by weight.

Also preferably, the content of the peroxide (g) in the cement composition (B) is from 0.01 to 10% by weight, more preferably from 0.1 to 5% by weight. Not only one but also two or more different types of peroxides (g) may be in the composition.

Also preferably, the content of the salt of an aromatic sulfinic acid (h) in the cement composition (B) is from 0.01 to 10% by weight, more preferably from 0.1 to 5% by weight. Not only one but also two or more different types of salts of aromatic sulfinic acids (h) may be in the composition.

Regarding its packages, the cement composition (B) may be divided into two packs: one is a liquid pack (C) that contains the polyalkenoic acid (c), the polymerizable monomer (e), water (f) and the peroxide (g), and the other is a powder pack (D) that contains the ion-leachable glass filler (d) and the salt of an aromatic sulfinic acid (h). The cement composition (B) may also be divided into two paste packs: one is a paste composition (E) that contains the polyalkenoic acid (c), the polymerizable monomer (e), water (f) and the peroxide (g), and the other is a paste composition (F) that contains the ion-leachable glass filler (d), the polymerizable monomer (e) and the salt of an aromatic sulfinic acid (h). In any case, it is desirable that the salt of an aromatic sulfinic acid (h) is not in the same pack or composition as that containing any of the polyalkenoic acid (c), the peroxide (g) and the acid group-having polymerizable monomer (a).

If desired, the cement composition (B) may contain the aromatic secondary amine and/or aromatic tertiary amine (b). In this case, however, it is desirable that the amine component (b) is not in the same pack or composition as that containing the peroxide (g).

The primer composition (A) and the cement composition (B) may optionally contain a non-leachable filler. The non-leachable filler may be any of inorganic fillers, organic fillers and their composites. The inorganic fillers include, for example, silica, silica-based minerals such as kaolin, clay, mica; and silica-based ceramics and glass additionally containing any of $Al_2O_3$, $B_2O_3$, $TiO_2$, $ZrO_2$, BaO, $La_2O_3$, $SrO_2$, CaO, $P_2O_5$. Especially preferred are lanthanum glass, barium glass, strontium glass. Also usable are crystalline quartz, hydroxyapatite, alumina, titanium oxide, yttrium oxide, zirconia, barium sulfate. The organic fillers may be of organic resin, including, for example, polymethyl methacrylates, polyamides, polystyrenes, polyvinyl chlorides, chloroprene rubber, nitrile rubber, styrenebutadiene rubber. Also employable herein are inorganic/ organic composite fillers, which may be prepared by dispersing a non-leachable glass filler in the organic resin, or by coating a non-leachable glass filler with the organic resin. If desired, the fillers may be previously surface-treated with any known surface-treating agent such as a silane coupling agent. The surface-treating agent includes, for example, vinyltrimethoxysilane, vinyltriethoxysilane, vinyltrichlorosilane, vinyltri($\beta$-methoxyethoxy)silane, $\gamma$-methacryloylpropyltrimethoxysilane, $\gamma$-glycidoxypropyltrimethoxysilane, $\gamma$-mercaptopropyltrimethoxysilane, $\gamma$-aminopropyltriethoxysilane.

For increasing the amount of the fluoride ions to be released from it, the cement composition (B) that constitutes the kit of the invention may contain any known water-soluble fluoride compound provided that it does not affect any distinct negative influence on the bonding power of the cured product of the cement composition. For example, the water-soluble fluoride compound is a water-soluble metal fluoride that includes lithium fluoride, sodium fluoride, potassium fluoride, rubidium fluoride, cesium fluoride, beryllium fluoride, magnesium fluoride, calcium fluoride, strontium fluoride, barium fluoride, zinc fluoride, aluminium fluoride, manganese fluoride, copper fluoride, lead fluoride, silver fluoride, antimony fluoride, cobalt fluoride, bismuth fluoride, tin fluoride, silver diammine fluoride, sodium monofluorophosphate, potassium titanium fluoride, fluorostannates, fluorosilicates. One or more of these may be used herein. Preferably, the metal fluoride to be added to the cement composition is ground into powder, or is coated with polysiloxane.

Also if desired, the primer composition (A) and/or the cement composition (B) may contain any known stabilizer, photopolymerization initiator, dye, and/or pigment.

The dental composition kit of the invention may be used, for example, as follows. The primer composition (A) is first applied to the surface of a tooth to be treated, and then optionally dried with a dental air syringe. In case where the tooth is restored, it is filled with a single paste of the cement composition (B). On the other hand, when a prosthesis such as a crown or an inlay is bonded to the tooth, a single paste of the cement composition (B) is put between the prosthesis and the tooth and the two are bonded to each other. In that manner, the tooth surface is contacted with the cement composition (B) via the primer composition (A). In that condition, therefore, a polymerization initiation system (three-component system) comprising the aromatic secondary amine and/or aromatic tertiary amine (b) in the primer composition (A) and the peroxide (g) and the salt of an aromatic sulfinic acid (h) in the cement composition (B) is formed in the bonding interface to initiate radical polymerization therein, and, as a result, the cured cement firmly bonds to the tooth or to both the tooth and the prosthesis.

EXAMPLES

The invention is described in more detail with reference to the following Examples, which, however, are not intended to restrict the scope of the invention.

Bonding Test:

The labial surface of a bovine mandibular anterior tooth was ground with #80-grit silicon carbide abrasive paper (by Nippon Kenshi Co. Ltd.) with running water being applied thereto, and its enamel or dentin was thereby flattened. Thus ground, tooth was put into a stainless ring with its flattened enamel or dentin surface being exposed out, and this was fixed in a dental composite resin therein, and the ground surface thereof was polished with abrasive paper of up to #1000-grit silicon carbide (by Nippon Kenshi Co. Ltd.) with running water being applied thereto. In that manner, the enamel or dentin surface of the tooth was smoothed. An adhesive tape (thickness: about 150 microns) with a hole having a diameter of 4 mm was stuck on the surface of the exposed enamel or dentin surface. The primer composition to be tested was first applied to the holed area with a brush, then left as it was for 30 seconds, and thereafter dried with an air syringe. After thus dried, it was not fluid. Next, a cylindrical Teflon mold having a diameter of 4 mm and a height of 2 mm was put just on the hole of the sample, and filled with a uniform paste of the cement composition to be tested. With that, the cement composition was left as it was for 3 minutes, and cured. Then, the Teflon mold was removed to release the test sample. The test sample was dipped in water at 37° C. for 24 hours. Using a universal testing machine (by Instron), the measurement of shear bond strength was made at a cross head speed of 2 mm/min. Eight test samples were prepared and tested for each kit, and the data were averaged to obtain the shear bond strength of the cured cement.

Examples 1 to 7, Comparative Examples 1 to 5

10-Methacryloyloxydecyl dihydrogen phosphate (MDP), 6-methacryloyloxyhexyl dihydrogen phosphate (MHP), 2-methacryloyloxyethyl phenyl hydrogen phosphate (Phenyl-P), glycerol phosphate dimethacrylate (GPDM) and 4-methacryloyloxyethyl ester of trimellitic acid (4-MET) were used for the acid group-having polymerizable monomer (a); and diethanol-p-toluidine (DEPT) was for the aromatic secondary amine and/or aromatic tertiary amine (b). The ingredients were blended in a ratio as in Table 1 below to prepare one-pack primer compositions A-1, A-2, A-3, A-4 and A-5.

On the other hand, polyacrylic acid having a mean molecular weight of 25,000 was used for the polyalkenoic acid (c); aluminofluorosilicate glass GM35429 (by Shott Glas) was for the ion-leachable glass filler (d); 10-methacryloyloxydecyl dihydrogen phosphate (MDP), 2-methacryloyloxyethyl phenyl hydrogen phosphate (Phenyl-P), 2,2-bis[4-[3-methacryloyloxy-2-hydroxypropoxy]phenyl]-propane (Bis-GMA), neopentyl glycol dimethacrylate (NPG) and 2-hydoxyethyl methacrylate (HEMA) were for the polymerizable monomer (e); benzoyl peroxide (BPO) was for the peroxide (g); and sodium benzenesulfinate (BSS) was for the salt of an aromatic sulfinic acid (h). The ingredients were blended in a ratio as in Table 2 below to prepare cement compositions C-1, C-2 and C-3.

The primer composition was combined with the cement composition as in Table 3 below, and tested for the bond strength of the cured cement. These are Examples 1 to 7. In the bonding test, a drop of the primer composition was put in a Dappen dish, then left as it was therein for 3 minutes, and thereafter applied to the surface of a test tooth. The bond strength of the cured cement to the enamel and the dentin of the test tooth was measured, and the results are given in Table 3.

In addition, other primer compositions B-1 and B-2 were formulated as in Table 1, and cement compositions D-1 and D-2 were as in Table 2. Singly or combined as in Table 4 below not satisfying the requirement of the invention, the compositions were tested for the bond strength of the cured cement. These are Comparative Examples 1 to 5. The bond strength of the cured cement to the enamel and the dentin of the test tooth was measured, and the results are given in Table 4. The results in Tables 3 and 4 confirm that the combination of the primer composition and the cement composition of the invention gives cured cement of high bond strength to both the enamel and the dentin of teeth.

TABLE 1

Blend Ratio of Ingredients of Primer Composition (wt. pts.)

|  | A-1 | A-2 | A-3 | A-4 | A-5 | B-1 | B-2 |
|---|---|---|---|---|---|---|---|
| MDP | 15 | — | 10 | — | — | — | 15 |
| MHP | — | 15 | — | — | — | — | — |
| Phenyl-P | — | — | — | 15 | — | — | — |
| GPDM | — | — | 15 | — | — | — | — |
| 4-MET | — | — | — | — | 20 | — | — |
| Water | 55 | 40 | 45 | 55 | 55 | 55 | 55 |
| Ethanol | — | 10 | 30 | — | 15 | — | — |
| HEMA | 20 | 25 | — | 20 | 10 | 20 | 20 |
| NPG | — | 10 | — | — | — | — | — |
| DEPT | 5 | 5 | 5 | 5 | 5 | 5 | — |

Abbreviations:
MDP: 10-methacryloyloxydecyl dihydrogen phosphate
MHP: 6-methacryloyloxyhexyl dihydrogen phosphate
Phenyl-P: 2-methacryloyloxyethyl phenyl hydrogen phosphate
GPDM: glycerol phosphate dimethacrylate
4-MET: 4-methacryloyloxyethyl ester of trimellitic acid
HEMA: 2-hydroxyethyl methacrylate
NPG: neopentyl glycol dimethacrylate
DEPT: diethanol-p-toluidine

TABLE 2

Blend Ratio of Ingredients of Cement Composition (wt. pts.)

|  |  | C-1 | C-2 | C-3 | D-1 | D-2 |
|---|---|---|---|---|---|---|
| Liquid Pack | Polyacrylic acid | 30 | 30 | 30 | 30 | 45 |
|  | MDP | 10 | — | — | 10 | — |
|  | Phenyl-P | — | 10 | — | — | — |
|  | Bis-GMA | 10 | 5 | 15 | 10 | — |
|  | NPG | — | 5 | — | — | — |
|  | HEMA | 10 | 10 | 15 | 10 | — |
|  | Water | 40 | 40 | 40 | 40 | 55 |
|  | BPO | 1 | 1 | 1 | 1 | — |
| Powder Pack | GM35429 | 200 | 200 | 200 | 200 | 200 |
|  | BSS | 3 | 3 | 3 | — | 1 |

Abbreviations:
MDP: 10-methacryloyloxydecyl dihydrogen phosphate
Phenyl-P: 2-methacryloyloxyethyl phenyl hydrogen phosphate
HEMA: 2-hydroxyethyl methacrylate
BPO: benzoyl peroxide
Bis-GMA: 2,2-bis[4-[3-methacryloyloxy-2-hydroxypropoxy]phenyl]propane
NPG: neopentyl glycol dimethacrylate
GM35429: aluminofluorosilicate glass (by Shott Glas)
BSS: sodium benzenesulfinate

TABLE 3

|  | Example 1 | Example 2 | Example 3 | Example 4 | Example 5 | Example 6 | Example 7 |
|---|---|---|---|---|---|---|---|
| Primer Composition | A-1 | A-1 | A-1 | A-2 | A-3 | A-4 | A-5 |
| Cement Composition | C-1 | C-2 | C-3 | C-1 | C-1 | C-2 | C-3 |
| Bond Strength to enamel (MPa) | 19.2 | 18.7 | 16.3 | 16.8 | 17.8 | 22.3 | 15.3 |
| Bond Strength to dentin (MPa) | 17.2 | 17.6 | 13.2 | 14.9 | 16.5 | 15.8 | 12.0 |

TABLE 4

|  | Comp. Ex. 1 | Comp. Ex. 2 | Comp. Ex. 3 | Comp. Ex. 4 | Comp. Ex. 5 |
|---|---|---|---|---|---|
| Primer Composition | no | B-1 | B-2 | A-1 | B-1 |
| Cement Composition | C-1 | C-2 | C-1 | D-1 | D-2 |
| Bond Strength to enamel (MPa) | 8.3 | 1.2 | 7.7 | 9.0 | 1.3 |
| Bond Strength to dentin (MPa) | 6.8 | 1.5 | 3.8 | 4.2 | 0.8 |

Comparative Example 6

A two-pack primer composition of E-1-I and E-1-II was prepared, which corresponds to the primer composition A-2 in Example 4 but additionally contains an organic peroxide and a salt of a sulfinic acid.

| E-1-I Pack: | |
|---|---|
| MHP | 30 parts by weight |
| HEMA | 50 parts by weight |
| NPG | 20 parts by weight |
| BPO | 1.5 parts by weight |
| E-1-II Pack: | |
| Water | 80 parts by weight |
| Ethanol | 20 parts by weight |
| DEPT | 10 parts by weight |
| BSS | 1.5 parts by weight |

The composition was tested for the bond strength thereof in the same manner as in the previous Examples, except that the E-1-I pack and the E-1-II pack were mixed in a ratio of 1/1 in a Dappen dish. This is Comparative Example 6. While the mixture of the two packs was left as it was for only 3 minutes in the Dappen dish, its viscosity increased and the mixture became difficult to apply to teeth. In addition, the bond strength of the cured composition to the tooth enamel was 4.4 MPa, and was 3.4 MPa to the tooth dentin. The data are significantly lower than those in the Examples.

What is claimed is:

1. A dental composition kit comprising a combination of (A) a one-pack primer composition that contains (a) an acid group-having polymerizable monomer and (b) an aromatic secondary amine and/or an aromatic tertiary amine, and (B) a cement composition that contains (c) a polyalkenoic acid, (d) an ion-leachable glass filler, (e) a polymerizable monomer, (f) water, (g) a peroxide and (h) a salt of an aromatic sulfinic acid.

2. The dental composition kit according to claim 1, wherein the content of the acid group-having polymerizable monomer (a) in the primer composition (A) is from 1 to 90% by weight and the content of the aromatic secondary amine and/or aromatic tertiary amine (b) therein is from 0.1 to 20% by weight, and in the cement composition (B), the content of the polyalkenoic acid (c) is from 0.5 to 50% by weight, the content of the ion-leachable glass filler (d) is from 10 to 90% by weight, the content of the polymerizable monomer (e) is from 1 to 70% by weight, the content of water (f) is from 1 to 50% by weight, the content of the peroxide (g) is from 0.01 to 10% by weight and the content of the salt of an aromatic sulfinic acid (h) is from 0.01 to 10% by weight.

3. The dental composition kit according to claim 1, wherein the acid group-having polymerizable monomer (a) is a polymerizable monomer of the following general formula (I):

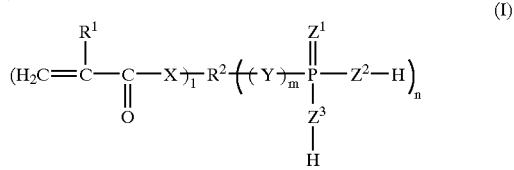

(I)

wherein R¹ represents a hydrogen atom or a methyl group; R² represents an organic group having from 2 to 40 carbon atoms; X represents a group of —O— or —NH—; l indicates an integer of from 1 to 5; m indicates an integer of 0 or 1; n indicates an integer of from 1 to 4; Y represents a group of —O— or —S—; and Z¹, Z² and Z³ each represent an oxygen at atom or a sulfur atom.

4. The dental composition kit according to claim 1, wherein the acid group-having polymerizable monomer (a) is a polymerizable monomer of the following general formula (II) and/or (III):

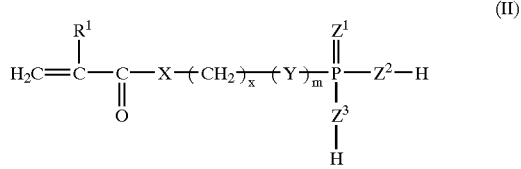

(II)

wherein R¹ represents a hydrogen atom or a methyl group; X represents a group of —O— or —NH—; x indicates an integer of from 4 to 20; m indicates an integer of 0 or 1; Y represents a group of —O— or —S—; and Z¹, Z² and Z³ each represent an oxygen atom or a sulfur atom;

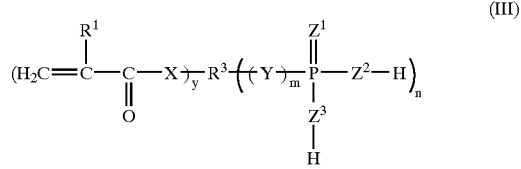

(III)

wherein R¹ represents a hydrogen atom or a methyl group; R³ represents an organic group having from 3 to 10 carbon atoms; X represents a group of —O— or —NH—; y indicates an integer of from 2 to 5; m indicates an integer of 0 or 1; n indicates an integer of from 1 to 4; Y represents a group of —O— or —S—; and Z¹, Z² and Z³ each represent an oxygen atom or a sulfur atom.

5. The dental composition kit according to claim 1, wherein the polyalkenoic acid (c) has a weight-average molecular weight of from 5,000 to 40,000.

6. The dental composition kit according to claim 1, wherein the ion-leachable glass filler (d) has a mean particle size of from 0.02 to 20 μm.

7. The dental composition kit according to claim 1, wherein the primer composition (A) additionally contains at least one of water and a volatile organic solvent having a boiling point not higher than 150° C.

8. The dental composition kit according to claim 1, wherein the primer composition (A) additionally contains a polymerizable monomer not having an acid group.

9. The dental composition kit according to claim 1, wherein the cement composition (B) is divided into two packs, wherein one pack is a liquid pack (C) that contains the polyalkenoic acid (c), the polymerizable monomer (e), water (f), and the peroxide (g), and the other pack is a powder pack (D) that contains the ion-leachable glass filler (d) and the salt of an aromatic sulfinic acid (h).

10. The dental composition kit according to claim 1, wherein the cement composition (B) is divided into two paste packs, wherein one pack is paste composition (E) that contains the polyalkenoic acid (c), the polymerizable monomer (e), water (f), and the peroxide (g), and the other pack is a pasty composition (F) at contains the ion-leachable glass filler (d), the polymerizable monomer (e), and the salt of aromatic sulfinic acid (h).

11. A method of using the dental composition kit according to claim 1, which comprises applying the primer composition (A) to the surface of a tooth to be treated, then filling said tooth with the cement composition (B), and then initiating radical polymerization, wherein the cement is cured and bonds to the tooth.

12. A method of using the dental composition kit according to claim 1, which comprises applying the primer composition (A) to the surface of the tooth to be treated, applying the cement composition (B) between the tooth and a prosthesis to be bonded to the tooth, and bonding the prosthesis to the tooth by initiating radical polymerization, wherein the cement is cured and bonds to both the tooth and the prosthesis.

* * * * *